United States Patent [19]

Groh et al.

[11] 4,417,353
[45] Nov. 22, 1983

[54] FAN BEAM CT SCANNER WITH COMPENSATING DETECTOR MOTION

[75] Inventors: Gunther Groh; Hermann Weiss, both of Hamburg; Wolfgang Wagner, Norderstedt; Klaus Pasedach, Hamburg; Gunter Kowalski, Hamburg; Dietrich Meyer-Ebrecht, Hamburg, all of Fed. Rep. of Germany

[73] Assignee: U.S. Philips Corporation, New York, N.Y.

[21] Appl. No.: 756,856

[22] Filed: Jan. 5, 1977

[30] Foreign Application Priority Data

Jan. 7, 1976 [DE] Fed. Rep. of Germany ....... 2600266

[51] Int. Cl.³ .............................................. G03B 41/16
[52] U.S. Cl. .......................................... 378/4; 378/19
[58] Field of Search .................. 250/445 T; 378/4, 19

[56] References Cited

U.S. PATENT DOCUMENTS

| | | | |
|---|---|---|---|
| 3,778,614 | 12/1973 | Hounsfield | 250/445 T |
| 3,934,142 | 1/1976 | Hounsfield | 250/445 T |
| 3,983,399 | 9/1976 | Cox | 250/445 T |
| 4,002,917 | 1/1977 | Mayo | 250/445 T |
| 4,010,370 | 3/1977 | Le May | 250/445 T |
| 4,057,725 | 11/1977 | Wagner | 250/445 T |

Primary Examiner—Craig E. Church
Attorney, Agent, or Firm—Jack E. Haken

[57] ABSTRACT

In fan beam X-ray scanners operating with a large number of detectors, errors at and near the center of rotation are caused by the fact that the radiation absorption in said area is substantially always measured by the same detectors and that the sensitivity of all detectors is not exactly the same. The invention provides an improvement in that the measurement is carried out with a larger number of detectors than is necessary for the measurement of the scanning field and that the detectors pivot during the measurement. As a result, the absorption in the center of rotation is measured by different detectors so that, for a sufficient number of detectors the different sensitivities, errors are averaged and thus reduced or cancelled.

10 Claims, 6 Drawing Figures

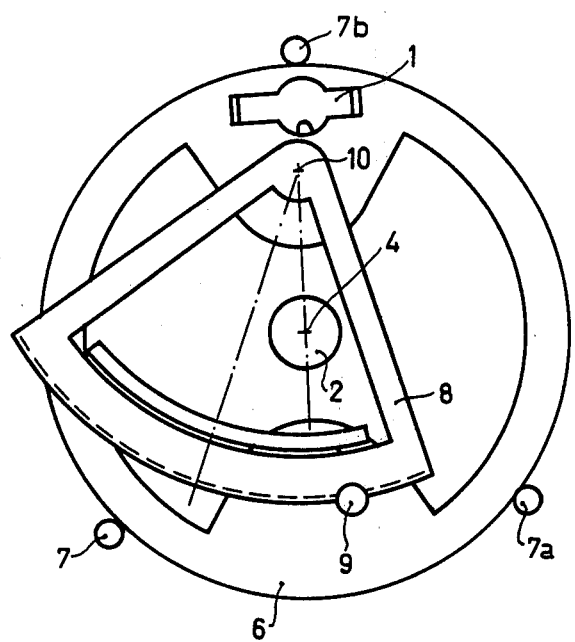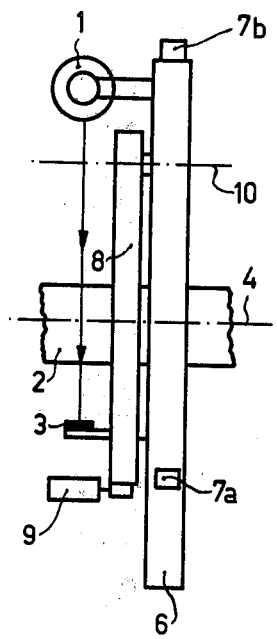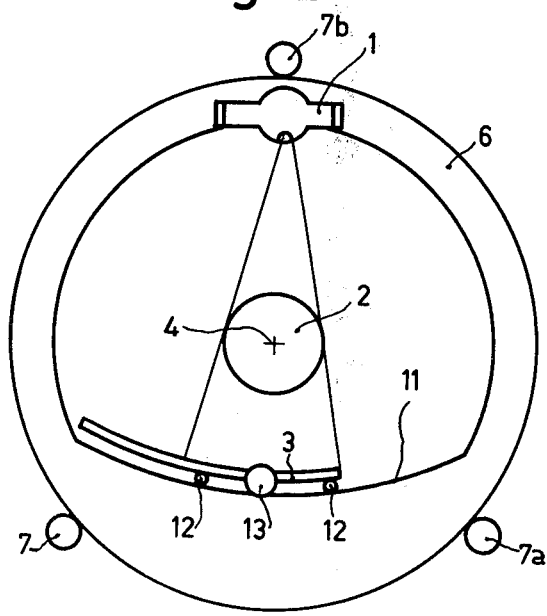
Fig. 2
Fig. 3
Fig. 4

FAN BEAM CT SCANNER WITH COMPENSATING DETECTOR MOTION

The invention relates to a device for measuring differences in radiation absorption in a plane of a body in of which a fan-like radiation beam passes through said plane of the body and is measured by a large number of detectors arranged on an arc of a circle in said plane. More specifically the invention relates to a device in which the detectors are disposed on an arc which is longer than is necessary for measuring the radiation behind the object and perform a pivoting motion about a center of curvature as the source-detector system is rotated with respect to the body during the measurement.

German Offenlegungsschrift No. 24 27 418, for example, discloses devices for measuring the absorption of radiation in a plane from a body comprising a source of which a fan-like radiation beam passes through said plane of the body and is measured by a number of detectors arranged in an arc of a circle in said plane and in which the source-detector system is rotated with respect to the body during the measurement.

The advantage of such a device as compared with a device having only one detector (for example German Offenlegungsschrift No. 19 41 433) is that the measurement can be performed more rapidly because a large number of measured values are obtained simultaneously and because the source-detector system has only to be rotated about an axis extending perpendicularly with respect to the plane of examination (which preferably extends through the body to be examined for a complete measurement). On the other hand, a drawback of this device is that as a result of the different sensitivities of the sources, errors may occur which may appear in the reconstruction of the image.

German Offenlegungsschrift No. 25 03 978 discloses a device of this kind and has for its object to reduce or remove said reconstruction errors. In this device, the source-detector system first performs a complete revolution during a measurement. At the beginning and at the end of said revolution the detectors measure the absorption of the body along the same stripe through the body. If the output signals of the various detectors differ from each other, the periodic change in the sensitivity can be calculated therefrom. The detectors are then rotated about the center of curvature of the arc of the circle on which they are arranged, so that each detector in a subsequent, second revolution measures the absorption along stripes through the body along which the absorption was measured in the preceding measurement by one of the two adjoining detectors. When the measured values supplied by a detector during the second revolution are compared with the measured values supplied by the adjoining detector during the first revolution, differences in sensitivity of adjoining detectors may be derived therefrom and be used for correcting of the measured values. The detectors are then returned to the position which they assumed during the first measurement, after which the system source-detector system is rotated for a third time and the absorption is measured again. By comparison with the measured values obtained during the second revolution, differences in the sensitivity of adjoining detectors and, by comparison of the measured values obtained at the beginning and at the end of the revolution, periodic fluctuations in the sensitivity of the individual detectors can again be determined.

The operation of this device is thus based on the fact that the absorption along each stripe through the body is measured several times. As a result of this, of course, time to obtain all the measured values is correspondingly extended and the dose which has to be supplied to the body to obtain said measured values also becomes correspondingly larger. Because this apparatus is used in particular for examining patients, this is a serious drawback. Another drawback of the known device is that the measured values change when the examined body varies its position during the measurement, These changed measured values are incorrectly evaluated by the device as a different sensitivity of adjoining detectors and as a drift phenomenon of the sensitivity of the individual detectors, respectively; as a result of this, extra errors occur in the reconstruction.

The invention is also of interest for the problem of avoiding and reducing, respectively, errors in the reconstruction occurring in a device having one source and a large number of detectors. However, in the first instance it concerns avoiding and removing, respectively, errors which occur to an intensified extent in the proximity of the center of rotation of the source-detector system, which center of radiation is as a rule present in the plane to be examined. Investigations which have also led to the present invention have demonstrated that these reconstruction errors are also determined by the different sensitivities of the individual detectors. Accordingly, it is the object of the invention to avoid or at least reduce the reconstruction errors in the proximity of the centre of radiation of the source-detector system without extending the measuring time or the dose and without extra reconstruction errors in the case of body movement during the measurement.

In order to reach the end in view, a device of the kind mentioned in the preamble is characterized in that the part of the arc of a circle provided excess detectors, is larger or not considerably smaller than the part necessary for the measurement of the radiation behind the object, that the pivoting motion takes place simultaneously with the rotary movement in such manner that during the rotation each detector measures the radiation behind the object once.

The expression "arc of a circle" may also be understood to be a straight line.

The invention will now be described in greater detail with reference to the drawing, in which:

FIGS. 2 and 3 show diagrammatically a first embodiment of a device according to the invention.

FIG. 4 is a diagrammatic representation of a further embodiment thereof.

Figure 1A:
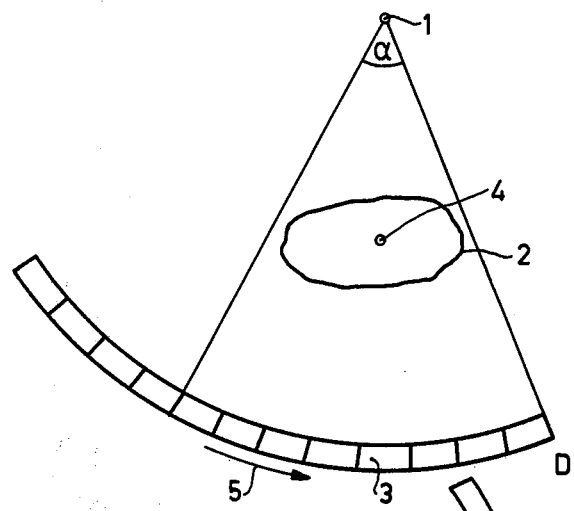
FIGS. 1a to 1c show a device according to the invention in various phases of the rotational and pivoting movements, respectively.

Referring now to the drawings, reference numeral 1 denotes a source, for example an X-ray tube. For simplicity, only a focus of the source is shown. The source comprises a collimator (not shown) which produces a beam of radiation which is narrow in the direction perpendicular to the plane of the drawing and is fan-like in the plane of the drawing. The extreme limits of said beam are denoted by solid lines starting from the focus of the source 1. The radiation passes through a body 2 of which the absorption distribution in the plane of examination is to be measured. The fan-like beam is measured by a group of detectors 3 which are arranged on an arc of a circle. The center of curvature of the arc of a circle on which the group of detectors 3 is arranged may coincide with the focus of the source 1 but may also be situated closer to the detector group or farther away therefrom dependent on the curvature of the arc. It is obvious from the drawings that the arc of the circle on which the detector group is arranged is considerably longer than is necessary for the measurement of the radiation behind the object or for the measurement of the maximum examination area which is defined by the extreme lines of the fan-like beam.

During the measurement, the source 1 and the group of detectors 3 rotate about an axis 4 which extends at right angles to the plane of the drawing and passes through the examination area. Superimposed upon said rotary movement, as denoted by the arrow 5, is an extra pivoting movement about a pivoting axis which also extends at right angles to the plane of the drawing and through the center of curvature of the arc of the circle. However, only the group of detectors 3 take part in the pivoting movement.

Figure 1B:
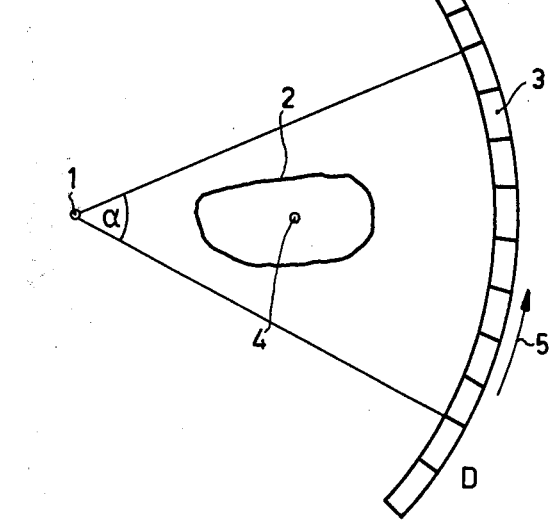
Figure 1C:
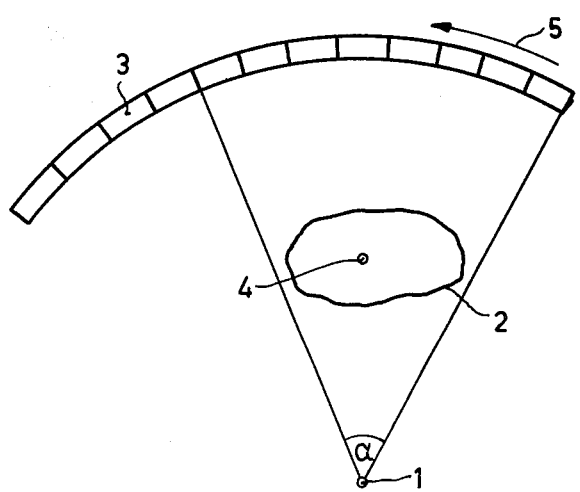

FIG. 1a shows the position of the device at the beginning of a measurement, FIG. 1b shows the position in which the measurement has progressed so that the source is rotated 90° about the axis of rotation 4, and FIG. 1c shows the position at the end of the measurement. It may be seen that in FIG. 1b the radiation is measured by a few detectors of the group which at the initial phase (shown in FIG. 1a) did not yet take part in the measurement, while a corresponding region of detectors in the central phase of FIG. 1b no longer takes part in the measurement. This is continued until, as is shown in FIG. 1c, the extreme right detector also takes part in the measurement.

As a result of the pivoting movement radiation, viewed with respect to the source, behind the center of rotation 4 is no longer measured by a single detector but by a large number of detectors in the various positions of the source 1. For example, if the number of the detectors necessary for measuring the fan-like beam is equal to 100 and if the detector group comprises 200, preferably equally large, detectors, then in the individual phases of the measurement the radiation behind the center of rotation is measured by 100 different detectors, (if the measurement at least a hundred measurements occur, and their angular positions are divided over equal angles). The different sensitivities of the individual detectors are summed in the reconstruction of the radiation absorption in the area of the center of rotation and provide a considerable reduction of the reconstruction error in the vicinity of the rotation center, because the deviations of their sensitivities from the exact value in general compensate each other (at least partly). This error becomes smaller as the ratio of the number of excess detectors to the number of detectors used in each measurement increases; that is as the part of the arc of the circle which is not necessary for the measurement is larger in comparison with the part necessary for the measurement. The length of this part and excess number of the detectors (not necessary for the measurement) should therefore be of the same order of magnitude as the length of the arc of the circle necessary for the measurement and the number of the detectors used for the measurement, respectively. Thus the total number of detectors must be substantially equal to or greater than twice the number of detectors necessary for the measurement. If said length is considerably smaller, for example, only a few detector widths, no significant improvement is obtained.

In the reconstruction of the absorption from the resulting measured results the fact that the absorption of the path of radiation which passes through the center of rotation was measured by different detectors should be taken into account and consequently measured values provided by different detectors should be assigned to said path of radiation. In the paths of radiation outside the center of rotation, but at a required distance therefrom, this is also the case and this should also be taken into account.

In the embodiment according to the invention shown in FIGS. 2 and 3 the source 1 is secured to an annular support 6 which is journalled on three bearings in such manner that it can be rotated about the axis 4 by means of a driving mechanism (not shown). The object 2 is also positioned in the vicinity of said axis. The group of detectors 3 is secured to a yoke 8 which is pivotable about the pivoting shaft 10 which extends at right angles to the plane of the drawing, passes through the center of curvature of the arc of the circle on which the detectors are arranged, and is secured to the annular support 6 by means of a driving mechanism 9. The driving mechanisms for the yoke 8 and for the annular support 6, respectively, are matched to each other in such manner that the yoke and the support perform the necessary pivoting and the rotation necessary of the measurement in the same period.

If, in the embodiment shown in FIGS. 2 and 3 collimators are used ahead of the detectors for suppressing parasitic radiation, contrary to what is shown in the drawing, the pivoting shaft and the centre of curvature, respectively, should coincide with the focus of the source. Thus, the collimators remain focused on the source in spite of the pivoting movement of the yoke.

When the detectors are arranged on an arc of a circle whose center of curvature coincides with the axis of rotation 4, only one driving motor for the rotary movement and the pivoting movement is necessary because the source and the detectors are rotated and pivoted, about the same axis of rotation although at different angular velocities. For that purpose, they may be coupled to the common driving motor via driving mechanisms having different transmissions.

It is furthermore favourable if the source is rotated about an axis extending perpendicular to the plane of the drawing and through the focus of the source synchronously with the pivoting movement. Reconstruction errors, if any, produced by a non-ideal source may thus be prevented. In fact, the radiation emitted by the source in the plane of the drawing does not have exactly the same intensity in all directions. Reconstruction errors caused by said inhomogeneous intensity distribution can be avoided in the known devices, (see for example the German Offenlegungsschrift No. 24 17 418), in that the sensitivity of the individual detectors is adjusted or readjusted each time so that the product of the detector sensitivity and the intensity of the part of the radiation measured by the detector is the same for all detectors. When the group of detectors is pivoted without correspondingly rotating the radiation cone, the individual detectors measure different parts of the radiation cone without it being possible to adapt the sensitivity of the detectors to the radiation cone. By the rotation of the source about the focus the individual detectors always cover the same area of the radiation cone so that the sensitivity of the detectors can be matched to it.

It is favorable when the center of curvature of the detector arc and the pivoting shaft, about which point said arc is pivoted, coincide with the focus of the source. The angular velocity of the rotary movement of the source about the focus thereof and the angular velocity of the arc of the circle about the pivoting shaft, that is about the focus, then are equal. In the embodiment shown in FIGS. 2 and 3 this has been achieved in that the source (1) is rigidly mounted on the yoke (8) so that the focus and the axis (10) coincide.

FIG. 4 shows another embodiment according to the invention which is specially suitable for devices in which the radius of curvature of the arc of the circle is very large (for example, when the detectors are located on a straight line and the radius of curvature thus is infinite). In this case the source 1 is also secured to an annular support 6 which can be rotated about its center 4 by means of the bearings 7 and a driving mechanism not shown. On its side opposite to the source the annular support 6 has a bearing surface 11 which has the same curavature as the arc of the circle on which the group of detectors 3 is arranged. The group of detectors 3 is moved over the bearing surface 11 during the measurement by means of the bearings 12 and a driving mechanism 13 shown diagrammatically.

What is claimed is:

1. In a device for measuring radiation absorption differences in a plane of a body wherein a source of radiation produces a fan-like beam of penetrating radiation which passes through the body and is measured by detectors in a detector group which is disposed on an arc of a circle; the source and detector group forming a system which rotates around the body so that the beam passes through the body from a plurality of angular orientations; the extent of the detector group being greater than the width of the fan-like beam whereby, at each angular orientation, a first subgroup of detectors in said group measure radiation which passes through said body and a second subgroup of detectors in said group do not measure radiation which passes through said body; the improvement wherein at each angular orientation the number of detectors in the second subgroup of detectors is substantially equal to or greater than the number of detectors in the first subgroup and further comprising means for pivoting the group about a center of curvature with a motion which is coupled to the rotation of the system so that individual detectors progressively move into and out of the radiation passing through the body at progressive angular positions and each detector in the detector group measures radiation passing through the body at some angular orientation.

2. A device as claimed in claim 1, wherein the pivoting and rotating movements occur continuously.

3. A device as claimed in claim 1, wherein the source is secured to a support which is rotatable about an axis of rotation perpendicular to the plane and the group of detectors is secured on a yoke which is journalled perpendicularly with respect to the plane, and is pivotable about a pivoting shaft connected to the support or a part rotated in the same sense.

4. A device as claimed in claim 1, wherein the source is secured to a support which is rotatable about an axis which is perpendicular with respect to the body plane, the support or a part connected thereto having a bearing surface which has the same curvature as the arc of the circle, in a second plane extending parallel with respect to the body plane and a part supporting the group of detectors is moveable over said bearing surface.

5. A device as claimed in claim 3, wherein the center of curvature of the arc of the circle and the pivoting axis, about which the detectors are pivoted during the measurement, coincides with a focus of the source.

6. A device as claimed in claim 1 wherein the source is rotatable about an axis extending perpendicular with respect to the body plane through a focus of the source, the angular velocity of the pivoting movement being chosen to be so that the part of a radiation cone emitted by the source and measured by the individual detectors does not vary as the detectors pivot.

7. A device as claimed in claim 2 wherein the pivoting and rotating movements have constant angular velocities.

8. A medical radiographic device for diagnostic examination of a substantially planar slice extending through the body of a patient, comprising:

a source of radiation arranged to project penetrating radiation substantially in the plane of the slice to traverse the body along a path determined by the position of the source relative to the body and to emerge therefrom after suffering absorption determined at least in part by that path;

a plurality of detector devices, some of which are irradiated by and measure the intensity of radiation traversing the body along the said path;

scanning means adapted to move said source relative to the body to project said penetrating radiation through the body along successive different paths each substantially coplanar with said slice, and means for moving said detector devices relative to said source and body so that for each of said paths at least one of said detector devices is different from those irradiated by radiation traversing other of said paths.

9. In radiation scanning apparatus wherein a source of radiation projects a planar, fan-like beam of radiation through a body to illuminate a multiplicity of radiation detector elements in a detector group, said source and said detector group rotating about said body as a coupled system, to successively project said beam through said body from a multiplicity of different angular orientations, the improvement wherein:

the extent of said beam is limited so that only a portion of the elements in said detector group is illuminated from each orientation and said apparatus further comprises means for progressively moving said detector group through said beam to progressively illuminate different elements in said group at successive angular orientations wherein the detector elements are disposed along an arc of a circle and said means for moving the detector group functions to pivot said detector group about an axis.

10. The apparatus of claim 9 wherein said axis approximately corresponds to a focal point of said source.

* * * * *